(12) United States Patent
Ascensao et al.

(10) Patent No.: US 12,004,538 B2
(45) Date of Patent: Jun. 11, 2024

(54) METHOD FOR IMPROVING MEAT QUALITY

(71) Applicant: CAN TECHNOLOGIES, INC., Wayzata, MN (US)

(72) Inventors: Alcina Ascensao, Nijmegen (NL); Brooke Humphrey, Maple Grove, MN (US); Ad Van Wesel, Made (NL)

(73) Assignee: CAN TECHNOLOGIES, INC., Wayzata, MN (US)

(*) Notice: Subject to any disclaimer, the term of this patent is extended or adjusted under 35 U.S.C. 154(b) by 0 days.

(21) Appl. No.: 17/815,650

(22) Filed: Jul. 28, 2022

(65) Prior Publication Data
US 2022/0361528 A1    Nov. 17, 2022

Related U.S. Application Data

(63) Continuation of application No. 16/625,238, filed as application No. PCT/US2018/038931 on Jun. 22, 2018, now Pat. No. 11,547,126.

(60) Provisional application No. 62/523,893, filed on Jun. 23, 2017.

(51) Int. Cl.
| | |
|---|---|
| *A23K 20/24* | (2016.01) |
| *A23K 50/30* | (2016.01) |
| *A23L 13/40* | (2023.01) |
| *A61K 33/06* | (2006.01) |

(52) U.S. Cl.
CPC .............. *A23K 20/24* (2016.05); *A23K 50/30* (2016.05); *A23L 13/432* (2016.08); *A61K 33/06* (2013.01); *A23V 2002/00* (2013.01)

(58) Field of Classification Search
CPC ........ A23K 20/24; A23K 50/30; A23K 20/22; A23K 50/60; A23L 13/432; A23L 13/40; A23V 2002/00; A61K 33/06
See application file for complete search history.

(56) References Cited

U.S. PATENT DOCUMENTS

| | | |
|---|---|---|
| 3,639,584 A | 2/1972 | Klenholz |
| 3,666,488 A | 5/1972 | Yukihiro |
| 6,514,521 B1 | 2/2003 | Julien |
| 7,105,191 B2 | 9/2006 | Mishra |
| 8,303,979 B2 | 11/2012 | Van Der Lende |
| 8,771,723 B2 | 7/2014 | Perdok |
| 2004/0234626 A1 | 11/2004 | Gardiner |
| 2004/0234650 A1 | 11/2004 | Mishra |
| 2006/0257537 A1 | 11/2006 | Claus |
| 2011/0313043 A1 | 12/2011 | Kramer |
| 2014/0099406 A1 | 4/2014 | Hoffmann Pegoraro |
| 2014/0227396 A1 | 8/2014 | Marcussen |
| 2017/0088477 A1 | 3/2017 | Morash |

FOREIGN PATENT DOCUMENTS

| | | |
|---|---|---|
| AU | 2013264002 B2 | 11/2016 |
| CN | 1144484 A | 3/1997 |
| CN | 103931907 A | 7/2014 |
| DE | 102007020378 A1 | 11/2012 |
| WO | 03009703 A1 | 2/2003 |
| WO | 2012159186 A1 | 11/2012 |
| WO | 2016090366 A1 | 6/2016 |
| WO | 2016177891 A2 | 11/2016 |

OTHER PUBLICATIONS

Thomas, Douglas D., et al., "The biological lifetime of nitric oxide: Implications for the perivascular dynamics of NO and O2", Proceedings of the National Academy of Science, Jan. 2, 2001, vol. 98, No. 1, pp. 355-360.
Tucker, T. M., et al., "Intrapartum Assessment of Fetal Well-Being", Clin. Obstet. & Gynecol. 33515. 1990. pp. 515-252.
Umans and Levi, "Nitric Oxide in the Regulation of Blood Flow and Arterial Pressure", Annu. Rev. Physiol. 1995. 57:771-90.
Webb, Andrew J., et al., "Acute blood pressure lowering, vasoprotective and anti-platelet properties of dietary nitrate via bioconversion to nitrite", Hypertension. Mar. 2008 ; 51(3): 784-790. doi:10.1161/HYPERTENSIONAHA.107.103523.
Wu, Guoyao, et al., "Impacts of arginine nutrition on embryonic and fetal development in mammals", Amino Acids (2013) 45:241-256.
Zhai Xiao-ju et al., "Advances in Using Nitride in Preventing Myocardial Ischemic-Reperfusion Injury", Adv Cardiovasc Dis, vol. 32, No. 4, pp. 582-586, published in Jul. 2011.
Bosi et al: "Effect of dietary addition of nitrate on growth, salivary and gastric function, immune response, and excretion of *Salmonella enterica* serovar Typhimurium, in weaning pigs challenged with this microbe strain", Italian Journal of Animal Science, vol. 6, No. Suppl. 1, Jan. 1, 2007 (Jan. 1, 2007), pp. 266-268.
Trevisi et al: "Effect of high oral doses of nitrate on salivary recirculation of nitrates and nitrites and on bacterial diversity in the saliva of young pigs: Oral nitrate, salivary nitrate and microbiota," Journal of Animal Physiology and Animal Nutrition. ,vol. 95, No. 2, Aug. 27, 2010 (Aug. 27, 2010), pp. 206-213.
Wu Qi, Carbon monoxide—an important biologically active molecule, Chemistry, Issue 5, Dec. 31, 1998, 38-43 [English translation included].
Yaping, et al., Antihypertensive effect mediated by nitrite and its mechanism, Science Bulletin, vol. 47, Issue 1, Jan. 31, 2002, 41-43. [English translation included].
(Lidder, S et al.) Vascular Effects of Dietary Nitrate (as Found in Green Leafy Vegetables and Beetroot) via the Nitrate-Nitrite-Nitric Oxide Pathway. British Journal of Clinical Pharmacology. 2012. vol. 75, No. 3; p. 677.
(Stahl, C) Research Spotlight. Swine News NC State University. Sep. 2008. vol. 31, No. 9, [Retrieved on Jan. 15, 2016]. Retrieved from the internet; URL: <https://www.ncsu.edu/project/swine_extension/swine_news/2008/september/september_08.pdf>.

(Continued)

*Primary Examiner* — Trevor Love

(57) ABSTRACT

The present invention relates to methods and compositions for improving the quality of meat obtained from an animal. In one aspect, the method relates to feeding an animal a diet containing calcium nitrate. In one aspect, the method relates to improving the redness of the meat color.

8 Claims, No Drawings

(56) References Cited

OTHER PUBLICATIONS (Wu, G et al.) Important Roles for the Arginine Family of Amino Acids in Swine Nutrition and Production. Livestock Science. 2007. vol. 112.
AASV, Basic Pig Terms, (2012), AASV, pp. 1-11 (Year: 2012).
Adriana Penuela S. et al., "Characterization of embryonic mortality in broilers", Rev.MVZ Cordoba, 23(1):6500-6513, 2018. ISSN: 0122-0268.
Alonso-Spilsbury, Maria et al., Perinatal asphyxia pathophysiology in pig and human: a review. Animal reproduction science 90 (2005) 1-30.
Asghar Ghasemi, "Review article: Quantitative Aspects of Nitric Oxide Production From Nitrate and Nitrite", Excli Journal 2022;21:470-486—ISSN 1661-2156.
Baxter, E.M. et al., "Investigating the behavioural and physiological indicators of neonatal survival in pigs", Theriogenology 69 (2008 )773-783.
Bouwkamp, et al., 1988, Tijdschr Diergeneesk. 113 (13), 737-747.
Brotanek, Vladimir, M.D., et al., "Changes in uterine blood flow during uterine contractions", Am. J. Obstet. Gynecol. 103:8; 1108 (1969).
Bruckdorfer, Richard "The basics about nitric oxide", Molecula Aspects of Medicine 26 (2005) 3-31.
Dantzer, Vibeke, "Electron microscopy of the initial stages of placentation in the pig", Anat Embryol (1985), 172:281-293.
Dougall, Hamish T., et al., "The effect of amoxycillin on salivary nitrite concentrations: an important mechanism of adverse reactions?" Br J Clin Pharmac 1995; 39:460-462.
Duncan, Callum, et al., "Chemical generation of nitric oxide in the mouth from the enterosalivary circulation of dietary nitrate", Nat Med 1:6; 546-551, Jun. 1995.
Dyck, G., et al., "Causes of Piglet Death From Bith to Weaning", Can. J. Anim. Sci. 67: 543-547 (Jun. 1987).
Feng, Zhanyu et al. "Application of an N-Carbamylglutamate, arginine endogenous activator, in Swine production", Swine Production, No. 4, pp. 9-11 (Year: 2010).
Fraser, David, et al. "Farrowing behaviour and stillbirth in two environments: an evaluation of the restraint-stillbirth hypothesis", Applied Animal Behaviour Science 55 (1997) 51-66.
Friend, D. W., et al. "the Duration of Farrowing in Relation to the Reproductive Performance of Yorkshire Sows", Can. J. Comp. Med. Vet. Sci., vol. 26, Jun. 1962, pp. 127-130.
G.W. Froning et al: Color of Poultry Meat as Influenced by Dietary Nitrates and Nitrites, Poultry Science, vol. 48, No. 2, Mar. 1, 1969 (Mar. 1, 1969), pp. 668-674, XP055765517, Oxford ISSN: 0032-5791, DOI: 10.3382/ps.0480668.
Gagnon, Robert, "Placental insufficiency and its consequences", European Journal of Obstetrics & Gynecology and Reproductive Biology, 110 (2003) S99-S107.
Gemma Vilahur et al., "Polyphenol-enriched Diet Prevents Coronary Endothelial Dysfunction by Activating the Akt/eNOS Pathway", Rev Esp Cardiol. 2015;68(3):216-225.
Govoni, Micro, et al., "The increase in plasma nitrite after a dietary nitrate load is markedly attenuated by an antibacterial mouthwash", Nitric Oxide 19 (2008) 333-337.
Hazeleger, W., Smits C. and B. Kemp. 2007. Influence of nutritional factors on placental growth and piglet imprinting. Paradigms in Pig Science.editors: J. Wiseman, M.A. Varley, S. McOrist,B. Kemp. Nottingham University Press, 309-328.
Henriksen, Tore, et al., "The fetal origins hypothesis: placental insufficiency and inheritance versus maternal malnutrition in well-nourished populations", Acta Obstet Gynecol Scand 2002: 81: 112-114.
Jansson, Emmelie A., et al., "A mammalian functional nitrate reductase that regulates nitrite and nitric oxide homeostasis", Nat Chem Biol 4:7 (Jul. 2008) 411-417.
Jaturasitha et al., "The Effect of Gender of Finishing Pigs Slaughtered at 110 Kilograms on Performance, and Carcass and Meat Quality", ScienceAsia 32 (2006): 297-305.

Kilbride, A. L., et al., "A cohort study of preweaning piglet mortality and farrowing accommodation on 112 commercial pig farms in England", Preventive Veterinary Medicine 104 (2012) 281-291.
Kim, Sung Woo, et al., "Regulatory role for amino acids in mammary gland growth and milk synthesis", Amino Acids (2009) 37:89-95.
Larsen et al. "Dietary nitrate reduces resting metabolic rate: a randomized, crossover study in humans 1-3", Am J Clin Nutr 2014;99:843-50.
Le Cozler, Yannick, et al., "Factors associated with stillborn and mummified piglets in high-prolific sows", Animal Research, EDP Sciences, 2002, 51(3), pp. 261-268.
Li, Yuzhi, et al., "Pre-weaning mortality of piglets in a bedded group-farrowing system", J of Swine Health Prod. 2010; 18(2): 75-80.
Lundberg, Jon et al., "The nitrate-nitrite-nitric oxide pathway in physiology and therapeutics", Nature Reviews Drug Discovery, vol. 7 Issue 2, Feb. 2008 (Feb. 2008), DOI:10.1038/nrd2466.
Lundberg, Jon O. et al., "Nitrate and nitrite in biology, nutrition and therapeutics", Nature Chemical Biology, vol. 5, No. 12, Dec. 2009, pp. 865-869.
M. Siervo, et al., "Intentional weight loss in overweight and obese individuals and cognitive function: a systematic review and meta-analysis", International Association for the Study of Obesity, 12, 968-983, 2011.
Mainau, E., et al., "A behavioural scale to measure ease of farrowing in sows", Theriogenology 74 (2010) 1279-1287.
Malte Kelm "Nitric oxide metabolism and breakdown", Biochimica et Biophysica Acta 1411 (1999) 273-289.
Marchant, J. N., et al., "Timing and causes of piglet mortality in alternative and confarrowing systems", Veterinary Record (2000) 147, 209-214.
Mateo, R. D., et al., "Effects of dietary arginine supplementation during gestation and lactation on the performance of lactating primiparous sows and nursing piglets", J Anim Sci 2008, 86:827-835.
Modesto, M. et al. Strategies to augment non-immune system based defence mechanisms against gastrointestinal diseases in pigs. NJAS-Wageningen Journal of Life Sciences, v. 58, n. 3-4, p. 149-156, 2011.
Oliviero, Claudio, et al., "Environmental and sow-related factors affecting the duration of farrowing", Animal Reproduction Science 119 (2010) 85-91.
Pawlak-Chaouch et al., "Effect of dietary nitrate supplementation on metabolic rate during rest and exercise in human: a systematic review and a meta-analysis", Nitric Oxide 53 (2016) 65-76.
Pernoll, M. L., and Benson R. C. (Ed.). 1988. Current Obstetric and Gynecological Diagnosis and Treatment (6th Ed.). Appleton and Lange, Nonvalk, CT.
Perry, J. S., "The mammalian fetal membranes", J. Reprod. Fert. (1981) 62, 321-335.
Persson, E. 1996. Studies of the endometrium and placenta during early pregnancy in the pig. Publisher: SLU, Uppsala (Sweden).
Randall, G. C.B., et al., "Observations on parturition in the sow. II. Factors influencing stillbirth and perinatal mortality", Vet. Rec. (1972) 90:183-186.
Rhodes, P. M., et al., "The L-Arginine: Nitric Oxide Pathway is the Major Source of Plasma Nitrite in Fasted Humans", Biochemical and Biophysical Research Communications, vol. 209, No. 2, 1995 (Apr. 17, 1995), pp. 590-596.
Rocha et al., "A shortcut to wide-ranging biological actions of dietary polyphenols: modulation of the nitrate-nitrite-nitric oxide pathway in the gut", Food Funct., 2014, 5, 1646-1652.
Seerley, R. W et al. Effect of nitrate or nitrite administered continuously in drinking water for swine and sheep. Journal of Animal Science, v. 24, n. 4, p. 1014-10119, 1965.
Seideman, S.C., et al., "Factors associated with fresh meat color: a review", Journal of Food Quality 6.3 (Feb. 15, 1984): 211-237.
Senger, P. L., Pathways to pregnancy and parturition, "Placentas have different distributions of chorionic villi", Chapter 14, p. 306, 2005.

METHOD FOR IMPROVING MEAT QUALITY

CROSS-REFERENCE TO RELATED APPLICATIONS

This application is a Continuation of U.S. patent application Ser. No. 16/625,238, filed Dec. 20, 2019, which is a national phase of International Application No. PCT/US2018/038931, filed Jun. 22, 2018, which claims the benefit of U.S. Provisional Patent Application Ser. No. 62/523,893, filed Jun. 23, 2017, each of which is hereby incorporated by reference in its entirety.

BACKGROUND OF THE INVENTION

Feeding calcium nitrate and other ingredients to ruminants is one way to mitigate methane production. For example, U.S. Pat. No. 8,771,723 titled "Compositions for Reducing Gastro-Intestinal Methanogenesis in Ruminants" issued to Hindrik Bene Perdok et al. discloses one such method. Further, Van Den Bosch et al. (International Patent Application Publication No. WO 2016/090366, published Jun. 9, 2016) describes animal feed compositions containing a nitrate compound and methods for using such a composition in an animal's gestation phase and/or lactation phase to improve the health of offspring.

In humans, dietary nitrate, as presented in beetroot juice, has been shown to reduce blood pressure and the risk of adverse cardiovascular events in healthy individuals after a single dose of 500 ml of beetroot juice. It is hypothesized that nitrate might represent a source of vasoprotective nitric oxide (NO) via bioactivation (Webb et al. 2008). A non-enzymatic pathway for the generation of NO has been proposed (nitrate-nitrite-NO pathway) for humans. Dietary inorganic nitrate molecules may be reduced by facultative anaerobic bacteria on the dorsal surface of the tongue to nitrite which can be chemically and enzymatically be further reduced to NO (Lundberg et al. 2009). The endothelial isoform of the NO synthase uses arginine and molecular oxygen as precursors to tonically release NO in the endothelium, which is important for the control of vascular tone, smooth muscle growth, platelet aggregation and inflammation (Umans and Levi, 1995; Bruckdorfer 2005). This induces vasodilation and increased blood flow (Siervo et al. 2011; Kelm 1999).

SUMMARY OF THE INVENTION

Disclosed herein are methods and compositions for improving the quality of meat obtained from an animal. In one aspect, the method relates to feeding an animal a diet containing a nitrate compound, for example calcium nitrate. In one aspect, the method relates to improving the redness of the meat color.

In one embodiment, the method is a method for improving meat quality in an animal comprising: feeding an animal an amount of a nitrate compound effective to improve at least one meat quality characteristic of meat obtained from the animal. In one embodiment, the method is a method for improving the color of meat obtained from an animal comprising, feeding an animal a diet comprising an effective amount of nitrate, wherein the redness of the color of meat obtained from the animal is greater than the redness of the color of meat obtained from a control animal fed a diet that does not include an effective amount of nitrate. In one embodiment, the composition is an animal feed diet, comprising: an amount of nitrate effective for increasing the red color of meat obtained from the animal.

In some embodiments, the meat quality characteristic that is improved by the methods or compositions described herein is color. In one aspect, the color of the meat can be measured using methods established by the International Commission on Illumination (CIE), i.e., CIE L*a*b* color measurement. The a* parameter corresponds to the red and green color spectrum. Positive a* values indicate red color while negative a* values indicate green color. Accordingly, an a* value of a meat which is greater than the a* value for a control sample indicates that the color of the meat is more red than the color of the control sample. In some embodiments, the a* value of the CIE L*a*b* color measurement of the meat obtained from the animal is greater than the a* value for meat obtained from a negative control animal fed a diet without nitrate compound. In some embodiments, the a* value of the meat from the animal is at least 5%, at least 10%, at least 15%, at least 20%, at least 25%, at least 30%, at least 35%, or at least 40% greater than the a* value of meat from the negative control animal at about 24 hours after slaughter of the animal. In some embodiments, the a* value of the meat from the animal is at least 9.8 at about 24 hours after slaughter of the animal. In some embodiments, the redness of the meat is measured according to the CIE L*a*b* color space method, and the a* parameter of meat obtained from the animal is at least 5%, at least 10%, at least 15%, at least 20%, at least 25%, or at least 30% greater than the redness of meat obtained from an animal not fed a diet comprising an effective amount of nitrate.

In some embodiments, the animal is a monogastric animal. In some embodiments, the animal is swine. In some embodiments, the animal is in a post-weening phase. In some embodiments, the animal is in a growth phase. In some embodiments, the animal is in a finishing phase.

In some embodiments, the amount of nitrate fed to the animal is at least 0.01 wt % of the daily diet. In some embodiments, the amount of nitrate fed to the animal is at least 0.06 wt % of the daily diet. In some embodiments, the amount of nitrate fed to the animal is in the range of 0.05 to 0.1% of the daily diet. In some embodiments, the nitrate compound is calcium nitrate.

In some embodiments, the method is a method for improving meat quality in an animal comprising: feeding an animal an amount of a nitrate compound effective to improve at least one meat quality characteristic of meat obtained from the animal, wherein the meat from the animal has an a* value of a CIE L*a*b* color measurement of the meat obtained from the animal is at least 9.4 9.5, 9.6, 9.7, 9.8, or 9.9 at about 24 hours after slaughter of the animal. In some such embodiments, an effective amount of nitrate for improving the a* value can be in any of the following ranges: 0.01 to 0.07%, 0.05 to 0.07%, 0.05 to 0.08%, 0.05 to 0.1%%, 0.01 to 0.11%, 0.05 to 0.11%, 0.05 to 0.12%, 0.05 to 0.13%, 0.05 to 0.14%, 0.05 to 0.15%, 0.06 to 0.1%, 0.06 to 0.11%, 0.01 to 0.15%, 0.01 to 0.2%, 0.01 to 0.3%, 0.01 to 0.5%, 0.05 to 0.2%, 0.05 to 0.5%, or 0.05 to 1.0%. In some such embodiments, the a* value of the meat from the animal can be at least 5%, 10%, 15%, 20%, 25%, 30%, 35%, or 40% greater than the a* value of meat from the negative control animal at about 24 hours after slaughter of the animal.

In one aspect, the methods described herein can be used to improve carcass yield. In some embodiments, the method improves the carcass yield (%) of an animal fed an effective amount of nitrate compared to a control animal fed a diet without an effective amount of nitrate. In some embodiments, the carcass yield of the animal fed an effective amount of nitrate is at least 1%, at least 2%, or at least 3% greater than a control animal fed a diet without an effective amount of nitrate. In some embodiments, the carcass yield of the animal fed an effective amount of nitrate is at least 80%, at least 81%, at least 82%, or at least 83%.

It is also to be understood that the elements or aspects of any embodiment of the processes, methods, or compositions described above can be applied to any other embodiment, as would be understood by a person skilled in the art.

DETAILED DESCRIPTION

It is to be understood that the figures and descriptions of the present invention provided herein have been simplified to illustrate elements that are relevant for a clear understanding of the present invention, while eliminating other elements found in the related field(s) of art. Those of ordinary skill in the art would recognize that other elements or steps may be desirable or required in implementing the present invention. However, because such elements or steps are well known in the art or do not facilitate a better understanding of the present invention, a discussion of such elements or steps is not provided herein.

Unless defined otherwise, all technical and scientific terms used herein have the same meaning as commonly understood by one of ordinary skill in the art to which this invention belongs. As used herein, each of the following terms has the meaning associated with it as defined in this section.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 7 should be considered to have specifically disclosed subranges such as from 1 to 3, from 1 to 4, from 1 to 6, from 2 to 5, from 3 to 5, etc., as well as individual numbers within that range, for example, 1, 2, 3, 3.6, 4, 5, 5.8, 6, 7, and any whole and partial increments in between. This applies regardless of the breadth of the range.

Method for Improving Meat Quality

Described herein are methods for improving the quality of meat by feeding an animal a suitable quantity of a nitrate compound. In one aspect, the methods can be used to increase the redness of the meat color of an animal by feeding the animal calcium nitrate or another nitrate-containing compound during the growing and/or finishing stages. In some embodiments, the animal is a monogastric animal, including but not limited to a pig.

While not intending to be limited by any particular theory, it is believed that nitrate is a source for the biological messenger nitric oxide (NO) according to a non-enzymatic pathway for the generation of NO (nitrate-nitrite-NO pathway). Unlike arginine conversion to nitric oxide, nitrate conversion to nitric oxide via the nitrate-nitrite-NO pathway is not dependent upon oxygen levels. It is believed that the release of NO in the animal is important for the control of vascular tone, smooth muscle growth, platelet aggregation and inflammation. The release of NO in the animal, for example, in a grower-finisher pig fed a supplement containing a nitrate compound, is believed to induce vasodilation and increased blood flow and exchange of oxygen.

The term "vasodilation" (or vasodilatation) as used in this disclosure refers to the widening of blood vessels in the animal. Vasodilation results from relaxation of smooth muscle cells within the vessel walls, in particular in the large veins, large arteries, and smaller arterioles. When blood vessels dilate in the animal, the flow of blood is increased due to a decrease in vascular resistance. Vasodilation may be localized to a specific organ (depending on the metabolic needs of a particular tissue, as during stress), or it may be systemic (seen throughout the entire systemic circulation). The primary function of vasodilation is to increase blood flow in the body to tissues that need it most. This is often in response to a localized need of oxygen, but can occur when the tissue in question is not receiving enough glucose or lipids or other nutrients.

Based on the nitrate-nitrite-NO pathway, a potential mode of action of dietary nitrate on heat stress reduction was conceived, and it was hypothesized that the increase in blood flow would promote heat loss by the animal, which could result in a decrease in heat production. This decrease in heat production was expected to decrease the core body temperature (the body 'cools down') which subsequently could result in a continued feed intake and growth performance. Although improvements in heat loss promotion and associated effects were not observed in pigs in such studies, it was surprisingly found that nitrate supplementation in animal feed has significant effects on meat quality characteristics, specifically improved meat color. Van Den Bosch (WO 2016/090366, which is hereby incorporated by reference in its entirety) describes compositions and methods for improving the health of the offspring of a sow by feeding the sow nitrate-containing feed during the sow's gestation and/or lactation phase. However, Van Den Bosch does not describe the use of nitrate in later phases of life, for example during the growth and/or finishing phases. Further, Van Den Bosch does not describe the use of nitrate to improve the specific meat quality characteristics described herein, e.g., increasing the redness of meat.

Research conducted at Research farm Raalte the Netherlands under supervision of the National Health Service for animals (Bouwkamp et al., 1988, Tijdschr Diergeneeskd 113 (13), 737-747) showed that nitrate can be dosed safely until at least the level of 0.1% nitrate in swine feed. Trials performed in grower-finisher pigs at Raalte delivered nitrate in the water and showed no effect on hemoglobin or met-hemoglobin in the blood for pigs fed nitrate. However, no effect was found on meat and liver NO content and on meat color, smell or taste. Further, Cargill research has shown that in young piglets receiving a feed dose titration of 0.2, 0.4, 0.6, 0.8 and 1.0% calcium nitrate there are no adverse effects on performance, and that met-hemoglobin, even at the highest level of calcium nitrate inclusion, stayed well within levels considered as safe.

In one aspect, the nitrate compound used in the method described herein can be any suitable nitrate-containing compound. As would be understood by a person skilled in the art, a suitable compound is defined as any physiologically acceptable or tolerated nitrate compound. In some embodiments, the nitrate compound is well-soluble in water, i.e., the compound has sufficient solubility for bioavailability after administration to the animal. In some embodiments, the nitrate compound is an ionic nitrate compound, preferably an inorganic nitrate salt. Non-limiting examples of nitrate salts include sodium nitrate, potassium nitrate, calcium nitrate, magnesium nitrate, or ammonium nitrate, all of which are readily soluble in water at standard temperature and pressure. The salts can include different hydrated forms. The salts can also include double salts (e.g., calcium nitrate and ammonium nitrate). In some embodiments, a mixture of two or more different nitrate salts or salt forms can be used in the method.

According to an exemplary embodiment, the nitrate is provided as inorganic calcium nitrate having the formula $Ca(NO_3)_2$. Calcium nitrate is also referred to as calcium dinitrate, Kalksalpeter, nitrocalcite, Norwegian saltpeter, and lime nitrate. Calcium nitrate may be produced by treating limestone with nitric acid, followed by neutralization with ammonia according to the reaction: $CaCO_3 + 2HNO_3 \rightarrow Ca(NO_3)_2 + CO_2 + H_2O$.

A variety of related complex inorganic salts of calcium nitrate include calcium ammonium nitrate decahydrate and calcium potassium nitrate decahydrate. Calcium ammonium nitrate is a double salt (calcium nitrate and ammonium nitrate) having the formula $5Ca(NO_3)_2 \cdot NH_4NO_3 \cdot 10H_2O$. According to an exemplary embodiment, the calcium ammonium nitrate is pentacalcium ammonium nitrate decahydrate commercially available from Bri-Chem Supply Limited with the following specification: Ammonium-N ($NH_4$—N) 1.1%; Nitrate-N ($NO_3$—N): 14.4%; Total N: 15.5%; Calcium (Ca): 18.8%. According to another exemplary embodiment, the calcium nitrate is BOLIFOR CNF calcium nitrate feed grade having the formula $5Ca(NO_3)_2 \cdot NH_4NO_3 \cdot 10H_2O$ commercially available from Yara Phosphates Oy of Helsingborg Sweden. According to an exemplary embodiment, the calcium nitrate can have the following specification: Calcium (Ca): 18.9%; Nitrogen (N) 15.5%; pH (10% solution): 6; bulk density kg/m3: 1050; appearance: prilled; size: <1.0 mm: 2%; 1.0-2.0 mm: 78%; >2 mm: 20%. Exemplary formulations of calcium nitrate lacking ammonia include $Ca(NO_3)_2 \cdot 4H_2O$. An exemplary anhydrous air-stable derivative of calcium nitrate includes the urea complex $Ca(NO_3)_2 \cdot 4[OC(NH_2)_2]$.

The nitrate compound may also be provided by a variety of plant ingredients according to alternative embodiments. Such plant ingredients may include, for example, leafy greens such as spinach, arugula and beetroot. Beetroot has an inorganic nitrate content typically ranging from 110 to 3670 mg nitrate/kg.

The amounts or levels of nitrate included in a feed or otherwise administered to the animal according to the method described herein correspond to nitrate ion amounts or levels. For example, Bolifor CNF™ calcium nitrate contains about 63% nitrate. As would be understood by a person skilled in the art, the amounts or levels of nitrate can be expressed as a mass or weight percent of nitrate compound by adjusting the mass or weight percent based on the total molecular weight of the nitrate compound, i.e., accounting for the portion of the compound other than the nitrate ion(s).

In one aspect, the level of nitrate fed to the animal in the method is an amount suitable, i.e., effective, for improving meat quality without producing deleterious effects in the animal. As described above, an amount of nitrate up to 0.1% is known to be safe in swine feed. Accordingly, in some embodiments, the amount of nitrate used in the method of the present invention can be 0.1% or less. However, it is contemplated herein that amounts of nitrate greater than 0.1% may be used safely in a feed diet for an animal. The maximum safe amount of nitrate for an animal feed can be readily determined by known methods in the art, based on factors including, but not limited to the type of animal and the age of the animal. In other embodiments, the amount of nitrate administered to the animal can be 0.5% or less, 0.4% or less, 0.3% or less, 0.2% or less, 0.15% or less, 0.09% or less, 0.08% or less, 0.07% or less, 0.06% or less, 0.05% or less, 0.04% or less, 0.03% or less, 0.02% or less, or 0.01% or less of an animal feed diet. In some embodiments, the amount of nitrate administered to the animal in the feeding methods and/or feed diet compositions can be in the range of 0.01 to 0.1%, 0.01 to 0.11%, 0.01 to 0.12%, 0.01 to 0.13%, 0.01 to 0.14%, 0.01 to 0.15%, 0.03% to 0.08%, 0.03 to 0.09%, 0.03 to 0.1%, 0.03 to 0.11%, 0.03 to 0.12%, 0.03 to 0.13%, 0.03 to 0.14%, 0.03 to 0.15%, 0.05 to 0.07%, 0.05 to 0.08%, 0.05 to 0.09%, 0.05 to 0.1%, 0.05 to 0.11%, 0.05 to 0.12%, 0.05 to 0.13%, 0.05 to 0.14%, 0.05 to 0.15%, 0.06 to 0.08%, 0.06 to 0.09%, 0.06 to 0.1%, 0.06 to 0.11%, 0.06 to 0.12%, 0.06 to 0.13%, 0.06 to 0.14%, 0.06 to 0.15%, 0.01 to 0.2%, 0.05 to 0.2%, 0.05 to 0.3%, 0.05 to 0.4%, or 0.05 to 0.5% of an animal feed diet. For the purposes of this disclosure, any of the above ranges can be considered to be an effective amount of nitrate for improving a meat quality characteristic such as color, including improving red color. Further, it is contemplated that a diet used as a control for reference purposes to compare to the compositions and methods of the present disclosure can contain some amount of nitrate (e.g., a trace amount) without such amount being considered an effective amount of nitrate.

In one aspect, the amount of nitrate administered to the animal can be expressed in terms of mg per kg of animal body weight per day. For example, the method can include providing to the animal less than 35 mg nitrate per kg of body weight of the animal per day, less than 30 mg nitrate per kg of body weight, less than 25 mg nitrate per kg of body weight, less than 20 mg nitrate per kg of body weight, less than 15 mg nitrate per kg of body weight, less than 10 mg nitrate per kg of body weight, or less than 5 mg nitrate per kg of body weight. The amount of nitrate in the feed (and the amount of nitrite) may be measured via ion chromatography. According to the ion chromatography method, samples are extracted with water, filtered, diluted and then applied to an anion exchange column. Nitrate is separated and identified using isocratic carbonate/bicarbonate elution coupled with suppressed conductivity detection. Concentration is determined using a standard curve of known nitrate solutions.

In another aspect, the amount of nitrate administered to the animal can be expressed in total mass per day. Accordingly, the nitrate compound can be fed to the animal such that the amount of nitrate fed per animal per day is less than 10 g nitrate, less than 5 g nitrate, less than 4 g nitrate, less than 3 g nitrate, less than 2 g nitrate, less than 1 g nitrate, or less than 0.5 g.

The method of improving meat quality can be used to improve at least one characteristic of meat quality. In some embodiments, the characteristic is color. In some such embodiments, the color improvement is an increase in redness of the meat. For example, cuts of meat having a high level of redness are often more desirable and/or are indicative of higher quality, and therefore more valuable than cuts of meat with less redness. In some geographic regions, for example some countries in Asia, more value is often placed on meats, for example pork, having a deeper or more apparent red color. Accordingly, in some embodiments, the methods and/or compositions described herein are useful for improving the quality of pork, e.g., the redness of the pork.

In some embodiments, the color characteristic can be evaluated using a color analyzer for measuring reflective colors of surfaces. These tools use the color differences one perceives to distances when measured colorimetrically. The a-axis measures the green (−a) to red (+a) spectrum, b-axis measures the blue (−b) to yellow (+b) spectrum and L measures brightness. These three measures create a three-dimensional model to more accurately define color perception of meat. In such a method, an increase in the a* parameter measured in a meat sample corresponds to an increase in redness. For the purposes of this disclosure and any related claims, an improvement or increase in the a* parameter of meat refers to a more positive value of the a* parameter, which corresponds to an increase in the redness of the color of the meat. As described above, the a* parameter can have a negative value (more green on the color spectrum) or a positive value (more red on the color spectrum). Accordingly, when a meat is described herein as having an a* parameter greater than a negative control sample, such description refers to a more positive (or less negative) a* value. Therefore, a meat referred to as having a greater a* parameter or a* value is more red in color than the control.

In some embodiments, the color characteristic can be evaluated using other methods, for example by comparing color templates corresponding to various levels of redness using a human tester, i.e., a visual scoring method, or a suitably configured computer or other testing machine. In one aspect, the improvements to meat quality can be more significant as time elapses after slaughter. For example, the improvement in the a* parameter of meat can be greater approximately 24 hours after slaughter than at the time of slaughter.

In one aspect, the a* value of the meat from the animal fed an effective amount of nitrate is at least 5%, at least 10%, at least 15%, at least 20%, at least 25%, at least 30%, at least 35%, or at least 40% greater than the a* value of meat from a negative control animal at about 24 hours after slaughter of the animal. As would be understood by a person skilled in the art, a negative control animal is an animal of the same species that has not been fed an effective amount of nitrate, but otherwise was raised substantially the same as an animal fed an effective amount of nitrate. Further, the improvements to meat quality may be more apparent after a time period longer than 24 hours, i.e., the meat from the negative control may lose color as time elapses, for example 36, 48, 60, 72, 84, or more hours after slaughter. Accordingly, meats produced using the methods described herein can have significantly better color characteristics at the time of purchase by a consumer, i.e., after time has elapsed to due shipping and/or packaging, than meats produced without an effective amount of nitrate.

In one aspect, the a* value of the meat from an animal administered an effective amount of nitrate is higher, i.e., more positive, than can be achieved without nitrate administration. In some embodiments, the a* value of the meat from an animal administered an effective amount of nitrate is at least 9.8 at about 24 hours after slaughter of the animal. In some embodiments, the a* value of the color of the meat from an animal administered an effective amount of nitrate is at least 9.3, 9.4, 9.5, 9.6, 9.7, 9.9, or 10.0 about 24 hours after slaughter of the animal. In some embodiments, the a* value of the color of the meat from an animal administered an effective amount of nitrate is at least 8.0, 8.1, 8.2, 8.3, 8.4, 8.5, 8.6, 8.7, 8.8, 8.9, 9.0, 9.1, 9.2, 9.3, 9.4, or 9.5 about 12 hours after slaughter of the animal. In some embodiments, the a* value of the color of the meat from an animal administered an effective amount of nitrate is at least 9.3, 9.4, 9.5, 9.6, 9.7, 9.8, 9.9, or 10.0 about 36 hours after slaughter of the animal. In some embodiments, the a* value of the color of the meat from an animal administered an effective amount of nitrate is at least 9.4, 9.5, 9.6, 9.7, 9.8, 9.9, or 10.0 about 48 hours after slaughter of the animal. In some embodiments, the a* value of the color of the meat from an animal administered an effective amount of nitrate is at least 9.4, 9.5, 9.6, 9.7, 9.8, 9.9, or 10.0 about 72 hours after slaughter of the animal.

The method of improving meat quality described herein can be used for monogastric animals, for example swine. In some embodiments, the method can also be used in other types of animals, for example ruminants, including cattle.

In one aspect, the nitrate is administered to the animal via feed, as described above. However, in other embodiments, a nitrate compound can be administered via other methods or routes, for example in a supplement pill or bolus, or via drinking water.

In another aspect, the methods described herein can be used to improve carcass characteristics. For example, the use of the methods can result in improvements to backfat, muscle, and/or lean meat percent compared to an animal not administered a nitrate compound.

In some embodiments, use of the methods result in higher carcass weight. In some embodiments, the carcass weight of an animal fed an effective amount of nitrate can be at least 1%, 2%, 3%, 4%, 5%, 6%, 7%, 8%, 9%, or 10% greater than a control animal fed a diet without an effective amount of nitrate.

In some embodiments, the methods can result in improvements to carcass yield. In some embodiments, the carcass yield of an animal administered a nitrate compound is at least 80%, 81%, 82%, 83%, 84%, or 85%. In some such embodiments, a control animal administered the same diet without inclusion of a nitrate compound will have a carcass yield significantly lower, for example less than 80%. In some embodiments, the carcass yield of the animal administered an effective amount of nitrate is at least 1%, 2%, 3%, 4%, 5%, 6%, 7%, 8%, 9%, or 10% greater relative to the carcass yield of a control animal fed a diet without an effective amount of nitrate.

Feed Diet Composition

In another aspect, the present invention relates to animal feed diet compositions and/or animal feed supplement compositions including an amount of nitrate suitable for improving one or more meat quality characteristics. In some embodiments, the feed diet composition includes 0.5% or less, 0.4% or less, 0.3% or less, 0.2% or less, 0.15% or less, 0.1% or less, 0.09% or less, 0.08% or less, 0.07% or less, 0.06% or less, 0.05% or less, 0.04% or less, 0.03% or less, 0.02% or less, or 0.01% or less of an animal feed diet. In some embodiments, the amount of nitrate in the feed diet composition is in the range of 0.01 to 0.1%, 0.05 to 0.1%, 0.06 to 0.1%, 0.05 to 0.15%, or 0.05 to 0.2% of an animal feed diet. Other ranges or amounts of nitrate useful in the present invention are described above in relation to methods and are applicable to both methods and compositions of the present invention.

In one aspect, the animal feed supplement is a composition containing nitrate that can be fed or administered to the animal before, during, or after providing the animal the feed diet, i.e., the nitrate is provided in a supplement separately from the feed diet or is provided in a supplement that is mixed with the feed diet. As would be understood by a person skilled in the art, the amount of nitrate in the supplement would typically be different from the final feed diet, i.e., the supplement includes a higher concentration of nitrate than the final diet itself.

The animal feed diet is the vehicle to deliver nutrients to the animal. Accordingly, the feed diet composition can include other nutrients. There are six major classes of nutrients: carbohydrates, fats, proteins, vitamins, minerals, and water. These nutrient classes can be categorized as either macronutrients (needed in relatively large amounts) or micronutrients (needed in smaller quantities). The macronutrients are carbohydrates, fats, fiber, proteins, and water. The micronutrients are minerals and vitamins. The macronutrients (excluding water) provide structural material (amino acids from which proteins are built, and lipids from which cell membranes and some signaling molecules are built) and energy. Vitamins, minerals, fiber, and water do not provide energy, but are required for other reasons. Micronutrients include antioxidants and phytochemicals. Nutrients are delivered by sources of ingredients.

Macromineral (also referred to as bulk minerals) nutrients include, for example, calcium, chlorine (as chloride ions), magnesium, phosphorus, potassium, sodium, and sulfur. Micromineral (also referred to as trace minerals) nutrients include, for example, cobalt, copper, chromium, iodine, iron, manganese, molybdenum, nickel, selenium, vandadium, and zinc.

Vitamins nutrients include, for example, vitamin A. Ingredient sources of vitamin A include, for example, vitamin A supplement, vitamin A oil, etc. Vitamins also include, for example, vitamin B1, vitamin B2, vitamin B3, vitamin B4, vitamin B5, vitamin B6, vitamin B7, vitamin B9, vitamin B12, and vitamin C. Vitamins also include, for example, vitamin D. Ingredient sources of vitamin D include, for example, vitamin D supplement. Vitamins also include, for example, vitamin E. Ingredient sources of vitamin E include, for example, vitamin E supplement. Vitamins also include, for example, vitamin K. Other vitamin product ingredients may include, for example, riboflavin, vitamin D3 supplement, niacin, betaine, choline chloride, tocopherol, inositol, etc.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather should be construed to encompass any and all variations which become evident as a result of the teaching provided herein.

Example 1: Effect of Nitrate and Heat Stress on Swine

A trial was conducted to test two different levels of Bolifor™ CNFR (calcium nitrate) for its effect on technical performance and carcass characteristics, including pH and meat color, in both normal and high temperature conditions.

Based on the nitrate-nitrite-NO pathway it was hypothesized that the increase in blood flow could promote heat loss by the animal, which could result in a decrease in heat production. This decrease in heat production was expected to decrease the core body temperature which subsequently should result in a continued feed intake and growth performance in animals under heat stress. In addition, it was also hypothesized that, due to the increase in blood flow, a redder meat color would be seen in the group of pigs under nitrate level 0.1%.

No interaction effects between nitrate and temperature were observed for performance, carcass characteristics, and meat color (L*, a* and b*) and pH. Heat stress had a negative effect on technical performance. Pigs under heat stress reduced their average daily gain (ADG) and average daily feed intake (ADFI) (−5% and −7%, respectively) compared to pigs under thermo-neutral conditions. Significant difference was observed for L* and b* at 27 h post-mortem for main effect of temperature. Results indicate a PSE meat (pale, soft and exudative) for pigs under heat stress conditions; Minolta L* was 55 and ultimate pH was 5.35.

Regarding the effect of nitrate level, a significant difference was observed for a* at day 2 after slaughter. The parameter a* linearly increased with an increase in level of calcium nitrate in the diet. A redder meat color was found in the group of pigs fed nitrate level 0.1%.

MATERIALS AND METHODS

The trial was conducted in the grower-finisher unit 1 and 2 of Cargill Innovation Center Velddriel, The Netherlands. Pigs were allocated with 64 days of age. A randomized block design was used using 6 treatments divided over 48 pens by using 8 weight blocks in total. A pen was the experimental unit. Each pen contained 4 animals. Barrows and gilts were equally distributed among treatments. The experiment consisted of a 3×2 factorial design with three different levels of Bolifor™ CNFR (calcium nitrate) and with and without heat stress, with 8 replications per treatment (Table 1). During phase 1 (day 0 to day 24, i.e., d0-24) a common diet was fed. In phase 2 (d24-56) and phase 3 (d56-101) pigs were fed one of the 6 experimental diets (pellet form).

On day 83 of the trial one pig per pen was removed and transported to a commercial processing plant. On day 102, pigs were weighed and transported to a commercial processing plant (Compaxo, Zevenaar, The Netherlands). Each pig received an ear tag according to pen number to allow for data retrieval by pen and carcass data collection at the packing plant. Hot carcass weights (HCW) were measured immediately after evisceration and each carcass was evaluated for backfat, loin depth, and lean percentage. Fat depth and loin depth were measured with an optical probe inserted between 3rd and 4th last rib. Lean percentage was provided from the packing plant by using a proprietary equation. Percentage yield was calculated by dividing HCW by live weight obtained before transport to the packing plant.

TABLE 1

Experimental Design

| Treatment | Temperature | Description | Bolifor CNF* (kg/mton) | Nitrate (kg/mton) |
|---|---|---|---|---|
| 1 | Normal | Negative control (NC) | 0 | 0 |
| 2 | | NC + Ca(NO$_3$)$_2$ level 1_N | 1.00 | 0.63 |
| 3 | | NC + Ca(NO$_3$)$_2$ level 2_N | 1.58 | 1.00 |
| 4 | High | Negative control (NC) | 0 | 0 |
| 5 | | NC + Ca(NO$_3$)$_2$ level 1_N | 1.00 | 0.63 |
| 6 | | NC + Ca(NO$_3$)$_2$ level 2_N | 1.58 | 1.00 |

*Diets were formulated with Bolifor CNF, containing 63.12% of nitrate

Housing

Temperature, humidity and ventilation were automatically controlled. During phase 1 (from experimental day 0 until 24) pigs were not submitted to heat stress conditions. From experimental day 32 onwards pigs in Unit 2 were exposed to heat stress conditions (total period length of 66 days). During this period of heat stress the temperature was raised to 30° C. (from 8 AM-6 PM) and decreased to 26° C. from 6 PM-8 AM. During the heat stress period the relative humidity was kept at 80% in Unit 2 and the minimum ventilation was adjusted according to the body weight of the pigs. Temperature, humidity and ventilation settings in Unit 1 and 2 are presented in Table 2. Actual temperature, humidity and ventilation values did not deviate significantly from the settings during the trial.

TABLE 2

Temperature, humidity and ventilation during the trial

| Pigs age (d) | Exp. days | Temperature (° C.) Unit 1 | Temperature (° C.) Unit 2 Day* | Temperature (° C.) Unit 2 Night* | Humidity (%) Unit 1 | Humidity (%) Unit 2 | Min. Ventilation (%) Unit 1 | Min. Ventilation (%) Unit 2 |
|---|---|---|---|---|---|---|---|---|
| 63-72 | 0-9 | 24 | 24 | 24 | 50 | 50 | 10 | 10 |
| 72-78 | 9-15 | 22 | 22 | 22 | 50 | 50 | 10 | 10 |
| 78-84 | 15-21 | 21 | 21 | 21 | 50 | 50 | 10 | 10 |
| 84-91 | 21-30 | 20 | 20 | 20 | 50 | 50 | 10 | 10 |
| 92 | 31 | 20 | 22 | 22 | 50 | 50 | 10 | 18 |
| 93 | 32 | 20 | 24 | 24 | 50 | 50 | 10 | 18 |
| 94 | 33 | 20 | 26 | 26 | 50 | 50 | 10 | 18 |
| 95 | 34 | 20 | 28 | 26 | 50 | 50 | 10 | 18 |
| 96-162 | 35-101 | 20 | 30 | 26 | 50 | 80 | 10 | 23-28 (from day 70) |

*Day: 8 AM-6 PM/Night: 6 PM-8 AM

Diets

Batches of raw materials (Barley, Wheat, Soybean meal, Corn and Corn Dried Distillers Grains and Solubles (DDGS)) were reserved at the ABZ-Diervoeding production factory, Leusden, The Netherlands. Reserved batches were analyzed on crude protein, crude fat, crude ash, moisture, crude fibre (NIRS) and ICP at Provimi Rotterdam Laboratory, The Netherlands.

Formulation of diets was based on the analyzed nutrient content of the ingredients. A corn/soybean meal (SBM) basal diet was formulated and the nutrient profile was based on Grower-Finisher Shadow feeds for three phases with a market weight of 115 kg live body weight. Final experimental feeds were produced at ABZ-Diervoeding Leusden and delivered at GIC Velddriel. Diets are shown in Tables 3, 4, and 5.

TABLE 3

Experimental diet phase 1 (pre-grower)

| Ingredient | Amount (%) |
|---|---|
| Barley - Ground | 5.138 |
| Vleesvark. 0.75/0.5% | 0.75 |
| Limestone | 1.658 |
| L-Threonine | 0.007 |
| L-Lysine HCl | 0.206 |
| Monocalcium phosphate | 0.778 |
| Salt | 0.286 |
| Corn - Fine Ground | 40.133 |
| Sugarcane molasses SUG <47.5% | 1.0 |
| Soybean Meal - 48% Protein | 21.542 |

TABLE 3-continued

Experimental diet phase 1 (pre-grower)

| Ingredient | Amount (%) |
|---|---|
| Fat - Animal Blend | 1.0 |
| Corn DDGS | 7.5 |
| Wheat - Ground 8-14% NDF | 20 |

TABLE 4

Experimental diets phase 2 (d 24-56)

| | Amount (%) | | |
|---|---|---|---|
| Ingredient | NC | NC + $Ca(NO_3)_2$ level 1_N | NC + $Ca(NO_3)_2$ level 2_N |
| Bolifor CNF | 0.00 | 0.100 | 0.158 |
| Vleesvark. 0.75/0.5% | 0.75 | 0.75 | 0.75 |
| Limestone | 1.457 | 1.426 | 1.407 |
| Sunflower Meal 28% Protein | 4.00 | 4.00 | 4.00 |
| L-Threonine | 0.027 | 0.027 | 0.027 |
| L-Lysine HCl | 0.29 | 0.29 | 0.29 |
| Monocalcium phosphate | 0.829 | 0.786 | 0.761 |
| Salt | 0.385 | 0.385 | 0.385 |
| Corn - Fine Ground | 42.95 | 42.90 | 42.87 |
| Sugarcane molasses SUG <47.5% | 1.00 | 1.00 | 1.00 |
| Soybean Meal - 48% Protein | 14.68 | 14.69 | 14.69 |
| Fat - Animal Blend | 1.14 | 1.15 | 1.16 |
| Corn DDGS | 12.5 | 12.5 | 12.5 |
| Wheat - Ground 8-14% NDF | 20.0 | 20.0 | 20.0 |

TABLE 5

Experimental diets phase 3 (d 56-101)

| | Amount (%) | | |
|---|---|---|---|
| Ingredient | NC | NC + $Ca(NO_3)_2$ level 1_N | NC + $Ca(NO_3)_2$ level 2_N |
| Bolifor CNF | 0.00 | 0.100 | 0.158 |
| Vleesvark. 0.75/0.5% | 0.50 | 0.50 | 0.50 |
| Limestone | 1.167 | 1.119 | 1.090 |
| Sunflower Meal 28% Protein | 7.32 | 7.18 | 7.09 |
| L-Threonine | 0.003 | 0.002 | 0.002 |
| L-Lysine HCl | 0.349 | 0.348 | 0.347 |
| Monocalcium phosphate | 0.115 | 0.114 | 0.114 |
| Salt | 0.383 | 0.384 | 0.385 |
| Corn - Fine Ground | 41.542 | 41.544 | 41.546 |
| Sugarcane molasses SUG <47.5% | 1.00 | 1.00 | 1.00 |
| Soybean Meal - 48% Protein | 6.50 | 6.59 | 6.65 |
| Fat - Animal Blend | 1.00 | 1.00 | 1.00 |
| Corn DDGS | 20.0 | 20.0 | 20.0 |
| Wheat - Ground 8-14% NDF | 20.0 | 20.0 | 20.0 |

Measurements

Feed intake and body weight were measured at day 0, 24, 39, 59, 83 and 101. Ultrasound measurements were made at day 24, 59 and 101. To get more insight on metabolic defenses when pigs are submitted to heat stress, urine samples were taken at experimental day 84 (105 kg average BW) in the morning from the control animals (16 animals) in the heat stress group and the non-heat stressed group to measure pH, and calcium and phosphorus content. The pH was measured right after collection. During the first three weeks of heat stress skin temperature was measured daily with an infrared device (Testo 845). From 3 weeks onwards, skin temperature was measured weekly.

At slaughter, meat samples were taken to measure meat color. Color was evaluated at the longissimus muscle for L* (lightness), a* (redness), and b* (yellowness) values using a Minolta spectrophotometer. The first measurement was taken 3 hours postmortem and the second measurement 24 hours after first measurement. At the time of the 2nd color measurement, pH was also measured.

Statistics

For comparison of the different treatments, the parameters ADG, ADFI and Feed conversion ratio (FRC) (all normally distributed) were subjected to Mixed Model analysis, using SAS JMP (Version 9.0, SAS Institute Inc., Cary, NC, 2008) according to the following statistical model:

$$Y_{ijk} = \mu + \alpha i + \beta j + (\alpha\beta)ij + Sex_k + \delta i_1 + BW24_m + \varepsilon_{ijklm}$$

Where, $\mu$ = population mean;

$\alpha_i$ = main effect of temperature/room i (A), i=1, 2;

$\beta_j$ = main effect of calcium nitrate level j (B), j=1, 2, 3;

$Sex_1$ = random effect of sex, $_1$ = barrow, gilt;

$BW24_m$ = BW at day 24 (covariable)

$(\alpha\beta)_{ij}$ is the interaction effect of A and B; for each j and for each i $\delta_{ik}$ ~ Niid(0, $s^2a$) is the whole plot (block) error, k=1, 2, ..., 8;

$\varepsilon_{ijk}$ ~ Niid(0, $s^2e$) is the sub plot (pen) error, k=1, 2, ..., 8.

Linear and quadratic contrast for calcium nitrate level was tested. Differences between treatment means were assumed to be significant based on the probability of P<0.05 (Student t-test); unless other probability value is stated.

RESULTS

No interaction effects were observed between the temperature and the calcium nitrate level on weight, ADG and ADFI during the trial. For FCR, a tendency (P=0.09) was found for overall period (24-101 days), showing better FCR for the pigs under nitrate level 1 (0.063%) in heat stress conditions.

Heat stress had a negative effect on technical performance. Pigs under heat stress reduced their ADG, ADFI (−5% and −7%, respectively) and have shown better FCR during phase 3 (−3%; P<0.05) compared to the normal temperature and humidity conditions. Pigs were lighter by the end of the trial (d101; 2 kg lighter; P<0.05).

The calcium nitrate level had a quadratic effect on weight on day 83 and 101 (P<0.05). ADG tended to show a quadratic effect in phase 3 (d59-101; P<0.10) and showed a quadratic effect over the whole trial (d24-101; P<0.05). ADFI also showed a quadratic effect in phase 3 and over the whole trial (P<0.05). For efficiency two linear effects were observed. FCR linearly increased with an increasing in level of calcium nitrate in the diet in phase 2 (d24-59) and over the whole trial (d24-101; P<0.05).

TABLE 6A

Carcass characteristics

| | Temperature | | | | | |
| --- | --- | --- | --- | --- | --- | --- |
| | Normal | | | Heat stress | | |
| Treatment | NC | Nitrate 0.063% | Nitrate 0.1% | NC | Nitrate 0.063% | Nitrate 0.1% |
| Weight full, kg | 129.9 | 128.2 | 129.6 | 128.7 | 125.0 | 127.6 |
| Slaughter weight, kg | 127.2 | 126.0 | 127.3 | 125.9 | 122.8 | 124.9 |
| Carcass weight, kg | 101.3 | 105.1 | 99.5 | 100.3 | 100.2 | 101.2 |
| Backfat, mm | 19.5 | 20.3 | 16.8 | 18.6 | 18.7 | 18.9 |
| Muscle, mm | 66.1 | 67.8 | 69.3 | 69.4 | 68.6 | 68.5 |
| Lean meat, % | 55.4 | 55.0 | 57.4 | 56.2 | 56.1 | 55.9 |
| Carcass yield, % | 79.7 | 83.6 | 78.3 | 79.7 | 81.7 | 81.2 |

TABLE 6B

P values for carcass characteristics

| | Temp × Nitrate | Temp | Nitrate | Nitrate Linear | Nitrate quadr |
| --- | --- | --- | --- | --- | --- |
| Weight full, kg | 0.635 | 0.030 | 0.094 | 0.491 | 0.018 |
| Slaughter weight, kg | 0.642 | 0.011 | 0.123 | 0.696 | 0.046 |
| Carcass weight, kg | 0.099 | 0.236 | 0.269 | 0.751 | 0.113 |
| Backfat, mm | 0.116 | 0.881 | 0.196 | 0.250 | 0.596 |
| Muscle, mm | 0.124 | 0.168 | 0.520 | 0.991 | 0.504 |
| Lean meat, % | 0.927 | 0.968 | 0.515 | 0.267 | 0.703 |
| Carcass yield, % | 0.170 | 0.771 | 0.030 | 0.949 | 0.046 |

TABLE 7A

Meat color and pH

| | Temperature | | | | | |
| --- | --- | --- | --- | --- | --- | --- |
| | Normal | | | Heat stress | | |
| Treatment | NC | Nitrate 0.063% | Nitrate 0.1% | NC | Nitrate 0.063% | Nitrate 0.1% |
| L* day 1 | 41.7 | 42.5 | 43.0 | 43.8 | 43.1 | 42.5 |
| a* day 1 | 7.2 | 7.3 | 7.2 | 6.8 | 7.0 | 7.1 |
| b* day 1 | −1.6 | −1.5 | −1.4 | −1.5 | −1.5 | −1.6 |
| L* day 2 | 53.1 | 53.5 | 53.7 | 55.1 | 55.5 | 55.1 |
| a* day 2 | 9.3 | 9.8 | 9.9 | 9.3 | 9.5 | 9.8 |
| b* day 2 | −1.3 | −1.0 | −0.9 | −0.8 | −0.4 | −0.7 |
| pH* day 2 | 5.61 | 5.60 | 5.58 | 5.33 | 5.36 | 5.35 |

Day 1 = at the day of slaughter
Day 2 = 24 hours after slaughter

TABLE 7B

P values for Meat color and pH

|        | Temp × Nitrate | Temp  | Nitrate | Nitrate Linear | Nitrate quadr |
|--------|----------------|-------|---------|----------------|---------------|
| L* day 1 | 0.081 | 0.117 | 0.998 | 0.970 | 0.958 |
| a* day 1 | 0.731 | 0.078 | 0.573 | 0.296 | 0.937 |
| b* day 1 | 0.582 | 0.551 | 0.982 | 0.881 | 0.904 |
| L* day 2 | 0.774 | 0.000 | 0.814 | 0.640 | 0.674 |
| a* day 2 | 0.652 | 0.353 | 0.034 | 0.012 | 0.593 |
| b* day 2 | 0.478 | 0.001 | 0.064 | 0.081 | 0.115 |
| pH* day 2 | 0.763 | 0.000 | 0.757 | 0.796 | 0.487 |

As shown in Tables 6A and 6B, no interaction effects were observed between temperature and calcium nitrate level for carcass characteristics. There tended to be an interaction for carcass weight (P<0.10). The treatment with normal temperature and 0.063% calcium nitrate had a higher carcass weight, compared to the other treatments.

Temperature had an effect on full weight and slaughter weight (P<0.05). The pigs exposed to heat stress had a 2% lower full weight and slaughter weight. No significant effect for temperature was seen on carcass weight, back fat, muscle depth, lean meat percentage or carcass yield.

Regarding the effect of nitrate level, a quadratic effect was observed for full weight, slaughter weight and carcass yield of the pigs (P<0.05). The lowest slaughter weight was seen at 0.063% nitrate inclusion in feed, although carcass yield was the highest for the same treatment.

As shown in Tables 7A and 7B, no significant effects were observed for the pH values determined in longissimus dorsi when interaction and main effect of nitrate was studied. A significant difference (P=0.0001) was observed for temperature, showing the lowest pH in pigs under heat stress conditions (5.60 vs. 5.35).

To facilitate color communication, tools have been developed to aid in analyzing color, such has the CIE L*a*b* color space tool. In this system, color is expressed in a three dimensional space. A positive a* represents red, and a negative a* represents green (scale from +60 for red to −60 for green). A positive b* represents yellow, and a negative b* represents blue (scale from +60 for yellow to −60 for blue). The L* is represented numerically where 100 is white, and 0 is black. In present trial, there was no interaction between temperature and nitrate level for L*, a* and b* values. When main effect of temperature was studied, a significant difference was observed for L* (P=0.0001) and b* (P=0.001) at day 2 (27 h postmortem). Based on these results it can be concluded that temperature affects meat quality and will generate a PSE meat (pale, soft and exudative). Typical PSE-meat quality parameters are a Minolta L* higher than 50 (in this trial, the L* value was 55) and ultimate pH lower than 5.5 (Sellier and Monin 1994; PIC, 2003).

Regarding the effect of nitrate level, a significant difference was observed for a* at day 2 (P=0.012). The parameter a* linearly increased with an increasing in level of calcium nitrate in the diet. The lower a* and b* values in the negative control (a*=9.3 and b*=−0.8) indicate a low content of oxymyoglobin which is created in the oxidation process of myoglobin when exposed to air in meat (Jaturasitha et al., 2006, ScienceAsia 32: 297-305). Although no visual color measurements were taken, the significant effect seen from Minolta parameter a* in nitrate level indicates that nitrate might affect meat color—a redder meat color was found in the group of pigs fed nitrate level 0.1%.

Results from urinary pH, calcium and phosphorus did not show any significant differences between normal and heat stressed pigs under control treatment. Regarding skin temperature measurements, the heat stressed pigs had higher skin temperature compared to the pigs under normal conditions, although no interaction was found between temperature and the different nitrate levels.

CONCLUSIONS

No interaction effects between nitrate and temperature were observed for performance, carcass characteristics, and meat color (L*, a* and b*) and pH. Heat stress had a negative effect on technical performance. Pigs under heat stress reduced their ADG, ADFI (−5% and −7%, respectively) compared to pigs under thermo-neutral conditions.

Significant difference was observed for L* (P=0.0001) and b* (P=0.001) at day 2 indicating that heat stress can generate a PSE meat (pale, soft and exudative). Typical PSE-meat quality parameters are a Minolta L* higher than 50 (current trial=55) and ultimate pH lower than 5.5 (current trial=5.35).

Regarding the effect of nitrate level, a significant difference was observed for a* at day 2 (P=0.012). The parameter a* linearly increased with an increasing in level of calcium nitrate in the diet. A statistically significant redder meat color was found in the group of pigs fed nitrate level 0.1%.

The disclosures of each and every patent, patent application, or publication cited herein are hereby incorporated by reference in their entirety. While this invention has been disclosed with reference to specific embodiments, other embodiments and variations of this invention may be devised by others skilled in the art without departing from the true spirit and scope of the invention. The appended claims are intended to be construed to include all such embodiments and variations.

The invention claimed is:

1. A swine feed diet, comprising:
   an amount of nitrate effective for increasing the red color of meat obtained from the swine when fed during one or more of a post-weaning phase, growth phase, finishing phase, or combinations thereof of the swine; and
   the feed diet further comprises:
   1.090-1.658 wt % Limestone;
   0.002-0.027 wt % L-Threonine;
   0.207-0.349 wt % L-Lysine HCl;
   0.114-0.829 wt % Monocalcium Phosphate;
   0.286-0.385 wt % Salt;
   40.133-42.950 wt % Corn—Fine Ground;
   1.000 wt % Sugarcane Molasses<47.5%;
   6.500-21.542 wt % Soybean Meal—48% Protein;
   1.000-1.140 wt % Fat—Animal Blend;
   7.500-20.000 wt % Corn DDGS; and
   20.000 wt % Wheat—Ground 8-14% NDF;
   wherein the amount of nitrate is from 0.01 to 0.07%.

2. The feed diet of claim 1, wherein the amount of nitrate comprises a range of 0.02% to 0.07% nitrate.

3. The feed diet of claim 1, wherein the nitrate comprises calcium nitrate, sodium nitrate, potassium nitrate, magnesium nitrate, ammonium nitrate, or mixtures thereof.

4. The feed diet of claim 1, wherein the nitrate comprises calcium ammonium nitrate.

5. The feed diet of claim 1, wherein the nitrate comprises pentacalcium ammonium nitrate decahydrate.

6. The feed diet of claim 1, wherein the nitrate comprises plant ingredients selected from the group consisting of spinach, arugula, or beetroot.

7. The feed diet of claim 1, wherein the feed diet improves the redness of the color of meat obtained from swine fed the feed diet compared to the redness of the color of meat obtained from a control swine fed a diet without the amount of nitrate.

8. The feed diet of claim 7, wherein the redness of the meat is measured according to the CIE L*a*b* color space method, and the parameter of meat obtained from the animal is at least 30% greater than the redness of meat obtained from an animal not fed a diet comprising the amount of nitrate.

* * * * *